(12) United States Patent
Thennati et al.

(10) Patent No.: US 7,678,908 B2
(45) Date of Patent: Mar. 16, 2010

(54) PROCESS OF PREPARING DESALORATADINE

(75) Inventors: Rajamannar Thennati, Baroda (IN); Trinadha Rao Chitturi, Baroda (IN); Shivramchandra Kanangi, Baroda (IN); Raja Sekhar Unnam, Baroda (IN); Kanaksinh Jesingbhai Jadav, Baroda (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 293 days.

(21) Appl. No.: 10/510,619

(22) PCT Filed: Apr. 16, 2003

(86) PCT No.: PCT/IN03/00156

§ 371 (c)(1), (2), (4) Date: Oct. 7, 2004

(87) PCT Pub. No.: WO03/086275

PCT Pub. Date: Oct. 23, 2003

(65) Prior Publication Data

US 2006/0058334 A1 Mar. 16, 2006

(30) Foreign Application Priority Data

Apr. 15, 2002 (IN) .................... 348/MUM/2002

(51) Int. Cl.
*C07D 221/04* (2006.01)
*A61K 31/44* (2006.01)

(52) U.S. Cl. ....................... 546/93; 514/290

(58) Field of Classification Search .......... 546/93; 514/290

See application file for complete search history.

(56) References Cited

U.S. PATENT DOCUMENTS

| 4,659,716 A | 4/1987 | Villani et al. |
| 6,506,767 B1 | 1/2003 | Schumacher et al. |

FOREIGN PATENT DOCUMENTS

| WO | WO 85/03707 | * | 8/1985 |
| WO | WO 99/01450 | * | 1/1999 |
| WO | 02/42290 | | 5/2002 |

OTHER PUBLICATIONS

Fountoulakis et al, 1998, Hydrolysis and Amino acid compositions analysis.*

* cited by examiner

*Primary Examiner*—Rita J Desai
(74) *Attorney, Agent, or Firm*—Merchant & Gould P.C.

(57) ABSTRACT

The present invention provides substantially pure desloratadine having an HPLC purity greater than 99.5% and having an absorbance less than 0.15 Au at 420 nm for a 5% w/v solution in methanol, which does not show a peak for an impurity at a relative retention time in the range from about 0.85 to about 0.99 (relative to desloratadine appearing at a retention time of 25±5 minutes), which is greater than the discard limit set at less than 0.025% of the total area, when tested according to an HPLC method performed using a Hypersil BDS $C_8$ column (15 cm×4.6 mm, 5 µm particle size) with the following parameters:

| | |
|---|---|
| Mobile phase: | Buffer solution having a pH of about 3, methanol and acetonitrile in a volume ratio of 8:1:1. |
| Injection volume: | 20 µl |
| Flow rate: | 1.5 ml/minute |
| Run time: | 75 minutes. |
| Discard limit: | Set at less than 0.025% of total area |

The present invention also provides a process for the preparation of substantially pure desloratadine by the process comprising acidic hydrolysis of a compound of formula 3 where R is selected from $COR_1$, $COOR_1$ wherein $R_1$ is selected from branched or linear alkyl (1-6 C), cycloalkyl, alkenyl, alkynyl, aryl, aralkyl and their substituted analogs; and their substituted analogs with a strong organic acid or a mineral acid.

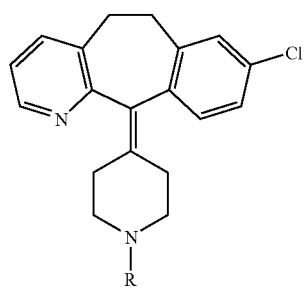

Formula 3

5 Claims, No Drawings

PROCESS OF PREPARING DESALORATADINE

FIELD OF THE INVENTION

The present invention relates to substantially pure desloratadine, a compound of formula 1, and a process of preparation thereof. Desloratadine, 8-chloro-6,11-dihydro-11-(4-piperidinylidene)-5H-benzo[5,6]cyclohepta[1,2-b]pyridine, is an antihistaminic agent useful in the treatment of seasonal allergic rhinitis.

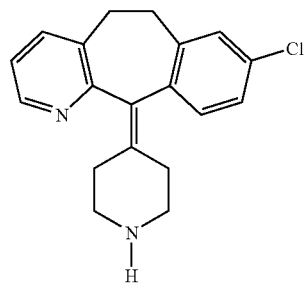

Formula 1

BACKGROUND OF THE INVENTION

The PCT publication WO 8503707 (hereinafter referred to as the '707 application, equivalent of which is the U.S. Pat. No. 4,659,716) claims desloratadine and exemplifies the process of its preparation by alkaline hydrolysis of loratadine (formula 2, scheme 1), followed by treatment with acetic acid to give the acetate salt of desloratadine, and then converting the acetate into the free base of desloratadine. However, the '707 application does not disclose the purity levels of desloratadine or its impurity profile.

Scheme 1

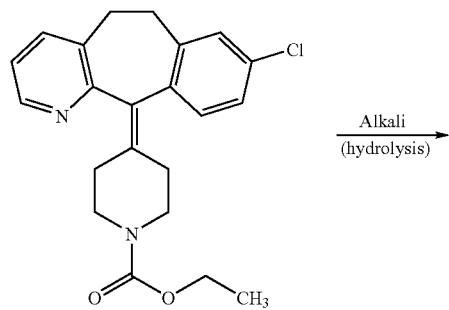

Formula 2

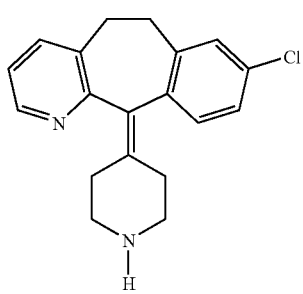

Formula 1

The PCT publication WO 9901450 (equivalent of which is the U.S. Pat. No. 6,506,767) discloses the polymorphic forms 1 and 2 of desloratadine. Preparation of the polymorphic forms 1 and 2 is disclosed by employing alkaline hydrolysis of loratadine by a process similar to that described in the '707 application, and then crystallization from methyl isobutyl ketone, hexanol, methanol, 3-methyl-1-butanol, cyclohexanol, chlorinated solvents such as dichloromethane, ethyl acetate and ether solvents such as dioxane, di-isopropylether, di-n-butylether. However, WO 9901450 too does not disclose the purity levels of desloratadine or its impurity profile.

The PCT application WO 02/42290 claims acid addition salts of desloratadine namely, monoacid, hemiacid and diacid salts. It discloses a process for preparation of diacid salts by reacting loratadine with concentrated mineral acids. It also teaches a process for conversion of diacid salts to monoacid or hemiacid salts by treatment with a solution of a base. It provides new desloratadine hemisulfate salt which is prepared from desloratadine disulfate salt with High Performance Liquid Chromatography (referred to as HPLC herein) purity greater than 99.5% by treatment with a solution of aqueous ammonia.

We have found that desloratadine when prepared according to the prior art processes shows a HPLC peak for an impurity at a relative retention time in the range from about 0.85 to about 0.99 (with respect to desloratadine), which is greater than the discard limit set at less than 0.025% of the total area, when tested according to an HPLC method performed using a Hypersil BDS $C_8$ column (15 cm×4.6 mm, 5 μm particle size) with the following parameters:

| | |
|---|---|
| Mobile phase: | Buffer solution having a pH of about 3, methanol and acetonitrile in a volume ratio of 8:1:1. |
| Injection volume: | 20 μl |
| Flow rate: | 1.5 ml/min |
| Run time: | 75 mins. |
| Discard limit: | Set at less than 0.025% of total area |

OBJECTS OF THE INVENTION

The object of the present invention is to provide substantially pure desloratadine and a process for preparation thereof.

A specific object of the present invention is to provide substantially pure desloratadine having an HPLC purity greater than 99.5%, and having an absorbance less than 0.15 Au at 420 nm for a 5% w/v solution in methanol.

A more specific object of the present invention is to provide substantially pure desloratadine which does not show a peak for an impurity at a relative retention time in the range from about 0.85 to about 0.99 (relative to desloratadine appearing at a retention time of 25±5 minutes), which is greater than the discard limit set at less than 0.025% of the total area, when tested according to an HPLC method performed using a Hypersil BDS $C_8$ column (15 cm×4.6 mm, 5 μm particle size) with the following parameters:

| | |
|---|---|
| Mobile phase: | Buffer solution having a pH of about 3, methanol and acetonitrile in a volume ratio of 8:1:1. |
| Injection volume: | 20 μl |
| Flow rate: | 1.5 ml/minute |
| Run time: | 75 minutes |
| Discard limit: | Set at less than 0.025% of total area |

More specifically, the object is to provide substantially pure desloratadine devoid or almost free of the said impurity and with total impurities less than 0.5%, preferably less than 0.3%, and no individual impurity greater than 0.1% and having UV absorbance less than 0.15 Au, preferably less than 0.10 Au at 420 nm for a 5% w/v solution in methanol.

Another object of the present invention is to provide a process for the preparation of substantially pure desloratadine which comprises acidic hydrolysis of a compound of formula 3 where R is selected from $COR_1$, $COOR_1$ wherein $R_1$ is selected from branched or linear alkyl (1-6 C), cycloalkyl, alkenyl, alkynyl, aryl, aralkyl and their substituted analogs; and their substituted analogs with a strong organic acid or a mineral acid.

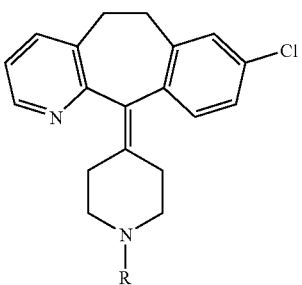

Formula 3

DETAILED DESCRIPTION OF THE PRESENT INVENTION

The present invention provides substantially pure desloratadine and a process for preparation thereof.

The substantially pure desloratadine of the present invention has an HPLC purity greater than 99.5% and having an absorbance less than 0.15 Au at 420 nm for a 5% w/v solution in methanol.

Substantially pure desloratadine of the present invention does not show a peak for an impurity at a relative retention time in the range from about 0.85 to about 0.99 (relative to desloratadine appearing at a retention time of 25±5 minutes), which is greater than the discard limit set at less than 0.025% of total area, when tested according to an HPLC method performed using a Hypersil BDS $C_8$ column (15 cm×4.6 mm, 5 µm particle size) with the following parameters:

| | |
|---|---|
| Mobile phase: | Buffer solution having a pH of about 3, methanol and acetonitrile in a volume ratio of 8:1:1. |
| Injection volume: | 20 µl |
| Flow rate: | 1.5 ml/minute |
| Run time: | 75 minutes |
| Discard limit: | Set at less than 0.025% of total area |

Relative retention time as referred to herein is the ratio of the retention time of the impurity to the retention time of desloratadine.

In preferred embodiment, the substantially pure desloratadine of the present invention is such that (a) total impurities are less than 0.5%; and (b) individual impurity is less than 0.1%.

Preferably substantially pure desloratadine according to the present invention is such that total impurities are not more than 0.3%, and has an absorbance less than 0.10 Au at 420 nm for a 5% w/v solution in methanol.

More preferably substantially pure desloratadine according to the present invention is such that total impurities are not more than 0.3%.

In the present invention substantially pure desloratadine when tested according to an HPLC method performed using a Hypersil BDS $C_8$ column (15 cm×4.6 mm, 5 µm particle size) with the following parameters:

| | |
|---|---|
| Mobile phase: | Buffer solution having a pH of about 3, methanol and acetonitrile in a volume ratio of 8:1:1. |
| Injection volume: | 20 µl |
| Flow rate: | 1.5 ml/minute |
| Run time: | 75 minutes |
| Discard limit: | Set at less than 0.025% of total area | is characterized by a peak at 25±5 minutes and does not show a peak for an impurity at a relative retention time in the range from about 0.85 to about 0.99 (with respect to desloratadine), which is greater than the discard limit set at less than 0.025% of the total area.

The present invention also provides a process for the preparation of substantially pure desloratadine.

The present invention provides a process for preparation of the substantially pure desloratadine comprising acidic hydrolysis of a compound of formula 3 where R is selected from $COR_1$, $COOR_1$ wherein $R_1$ is selected from branched or linear alkyl (1-6 C), cycloalkyl, alkenyl, alkynyl, aryl, aralkyl and their substituted analogs; and their substituted analogs with a strong organic acid or a mineral acid.

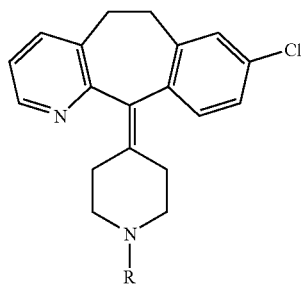

Formula 3

The substantially pure desloratadine may be prepared by acidic hydrolysis of a compound of formula 3 by heating with a strong organic acid or a mineral acid for a period of about 1 hour to about 24 hours. The temperature of reaction may vary from ambient to 150° C., preferably between about 60° C. to about 110° C. Examples of the organic acids include aqueous substituted and unsubstituted (C1 to C3) alkylsulfonic acids such as methanesulfonic acid, ethanesulfonic acid, halomethanesulfonic acids such as trifluoromethane sulfonic acid, fluoromethanesulfonic acid, chloromethanesulfonic acid, dichloromethanesulfonic acid, trichloromethane sulfonic acid and the like; substituted and unsubstituted aqueous arylsulfonic acids such as benzenesulfonic acid, para-toluenesulfonic acid, 4-chlorobenzenesulfonic acid and the like. Preferred organic acid is aqueous methanesulfonic acid, more preferably 90% methanesulfonic acid or greater than 90%. Examples of mineral acids include aqueous mineral acid such as halogen acids, phosphoric acid, polyphosphoric acid, perchloric acid, sulfuric acid and the like. The preferred mineral acid is aqueous sulfuric acid.

The hydrolysed reaction mixture is subjected to adjustment of pH between the range of about 3 to about 5, optional treatment with an adsorbent, adjustment of pH of the reaction mixture to a pH of about greater than 9 and isolation of desloratadine, for example by extraction with an organic solvent. The adsorbent is selected from charcoal, neutral or alkaline alumina, silica, fuller's earth and the like.

In a preferred embodiment the hydrolysed reaction mixture is subjected to adjustment of pH between the range of about 4 to about 5, optional treatment with charcoal, adjustment of pH of the reaction mixture to a pH of greater than about 9, preferably greater than about 9.5, and isolation of desloratadine, for example by extraction with an organic solvent.

The acidic hydrolysis process of the present invention may be carried out by heating with an acid for 1 about hour to about 24 hours at a temperature between the range of ambient to about 150° C., preferably between the range of about 60° C. to about 110° C.

In a preferred embodiment of the present invention, the compound of formula 3 is the one wherein R is $COOR_1$ and $R_1$ is ethyl i.e. the compound of formula 3 is 8-chloro-11-(1-carbonylethoxy-piperidin-4-ylidene)-6,11-dihydro-5H-benzo[5,6]cyclohepta[1,2-b]pyridine, and the organic acid used for acidic hydrolysis is methanesulfonic acid. The acidic hydrolysis reaction with methanesulfonic acid is preferably carried out for about 5 to about 15 hours at a temperature between the range of about 90° C. to about 120° C.

In another preferred embodiment of the present invention, the compound of formula 3 is the one wherein R is $COOR_1$ and $R_1$ is ethyl i.e. the compound of formula 3 is 8-chloro-1-(1-carbonylethoxy-piperidin-4-ylidene)-6,11-dihydro-5H-benzo[5,6]cyclohepta[1,2-b]pyridine, and the mineral acid used for acidic hydrolysis is sulphuric acid. The acidic hydrolysis reaction with sulphuric acid is preferably carried out for about 1 to about 5 hours at a temperature between the range of about 90° C. to about 120° C.

The desloratadine prepared by the process of the present invention may be further purified by recrystallization by dissolving desloratadine in a solvent mixture comprising two or more solvents, concentrating, cooling and isolating the substantially pure desloratadine by conventional means. The solvent system used in this step may comprise of two or more solvents selected from protic or aprotic solvents selected from water, alcohols, linear branched or cyclic hydrocarbons, aromatic hydrocarbons, ethers, ketones, nitrites, esters, and their halo or substituted analogs and the like, preferably the solvent system comprises a mixture of an alcohol like methanol and a hydrocarbon solvent like cyclohexane, more preferably the ratio of methanol:cyclohexane is 1:14 v/v.

The invention is further illustrated but not restricted by the description in the following examples.

EXAMPLES

Example 1

A mixture of 4-(8-chloro-5,6-dihydrobenzo[5,6]cyclohepta[1,2-b]pyridin-11-ylidene)piperidine-1-carboxylic acid ethyl ester (loratadine) (100.0 g, 0.26 mol), and 50% aqueous sulfuric acid (300 ml) was heated to 100-105° C. for 3 hrs. The reaction mass was cooled to ambient temperature and quenched into ice cold water (300 ml). The pH of the quenched mass was adjusted to pH 4.0 to 5.0 with liquor ammonia and charcoalized (5 g decolorizing charcoal). The pH of the charcoalized solution was adjusted to >9.5 with liquor ammonia, and sticky semi-solid mass which separated was extracted into toluene (700 ml). The toluene extract was concentrated under reduced pressure at below 65° C. and degassed to obtain an off-white to white solid of desloratadine (yield 78.0 g, 96%, purity >99.0%). HPLC analysis of the sample (as per the procedure described in example 2) did not show any peak due to impurity at relative retention time of 0.85 to 0.99 (relative to desloratadine peak).

The product obtained as above was dissolved in cyclohexane-methanol mixture (14:1, 750 ml) at 60-65° C., concentrated solution (to 550 ml) at atmospheric pressure and then cooled gradually to 10-15° C. Digested for 2 hrs at 10-15° C., filtered, and dried at 50-55° C. to obtain 8-chloro-11-piperidin-4-ylidene-6,11-dihydro-5H-benzo[5,6]cyclohepta[1,2-b]pyridine (desloratadine) (73 g, overall 90.0% yield, purity 99.92%. Absorbance at 420 nm for a 5% w/v solution in methanol is 0.032 Au).

Example 2

HPLC Analytical Method

Buffer:

Transfer 15.2 g of triethylamine into a 1000 ml volumetric flask. Dissolve in and dilute upto mark with HPLC grade water. Adjust the pH of the solution to 3.0±0.1 with 85% orthophosphoric acid.

Mobile Phase:

Mix buffer solution, methanol and acetonitrile in the ratio of 800:100:100. Filter and degas prior to use.

Sample Preparation:

Transfer about 50 mg accurately weighed sample into a 50 ml volumetric flask. Dissolve in and dilute upto mark with mobile phase.

System Suitability Solution:

Transfer about 20 mg of desloratadine into a 100 ml volumetric flask. Dissolve in and dilute upto mark with mobile phase Chromatographic System:

The liquid chromatograph is equipped with a 220 nm UV detector and 15 cm×4.6 mm, 5μ column that contains Hypersil BDS C8. The flow rate is about 1.5 ml/min.

Procedure:

Inject 20 μl of system suitability solution into the system and record the chromatograms upto 75 min. Calculate the tailing factor of desloratadine peak. It should not be more than 2 and number of theoretical plates should not be less than 3000.

Inject 20 μl of the sample preparation into the system and record the chromatogram upto 75 min. The retention time of desloratadine is 25±5 min. Calculate the amount of related substances by area normalization method, while disregarding any peak with an area percentage less than 0.025.

Desloratadine prepared according to the process of the present invention did not show a peak for an impurity at a relative retention time of 0.85 to 0.99 when tested according to the above method, however this impurity was found in desloratadine when prepared according to PCT publication Nos. WO 8503707 and WO 9901450.

Example 3

Loratadine Hydrolysis by Non-Mineral Acid

A mixture of 4-(8-chloro-5,6-dihydrobenzo[5,6]cyclohepta[1,2-b]pyridin-11-ylidene)piperidine-1-carboxylic acid ethyl ester (loratadine) (50.0 g, 0.13 mol), and 90% v/v aqueous methanesulfonic acid (165 ml) was heated to 105-110° C. for 9 hrs. The reaction mass was cooled to ambient temperature, quenched into water (300 ml) and the resulting solution heated at 90-100° C. for 1 hour. The reaction mixture was cooled to ambient temperature and extracted once with toluene (100 ml). The pH of the aqueous layer was adjusted between 4.0 to 5.0 with liquor ammonia and charcoalized (2.5 g decolorizing charcoal). The pH of the charcoalized solution was adjusted to >9.5 with liquor ammonia, and the sticky semi-solid mass which separated was extracted into toluene (300 ml). The toluene extract was concentrated under reduced pressure at below 65° C. and degassed to obtain an off-white to white solid of desloratadine (yield 40.5 g, purity >99.0%). HPLC analysis of the sample (as per the procedure described in example 2) did not show any peak due to impurity at relative retention time of 0.85 to 0.99 (relative to desloratadine peak).

The product obtained as above was purified from cyclohexane-methanol mixture (14:1, 750 ml) as in example-1 to obtain 8-chloro-11-piperidin-4-ylidene-6,11-dihydro-5H-benzo[5,6]cyclohepta[1,2-b]pyridine (desloratadine) (36.14 g, overall 89.0% yield, purity 99.96%. Absorbance at 420 nm for a 5% w/v solution in methanol is 0.067 Au).

Comparative Example

Tablet of Neoclarityn® (brand leader of desloratadine) containing 5 mg of desloratadine was crushed and powdered using pestle and mortar. The powder was taken up in 10 ml of the mobile phase (prepared as in example 2), sonicated for 10 mins. and filtered. HPLC chromatogram was recorded of this solution as per the procedure described in example 2. The chromatogram showed desloratadine at a retention time of 24.33 minutes, and an impurity at a relative retention time of 0.91 amounting to 0.12%.

We claim:

1. A process for preparation of desloratadine, the process comprising:
    heating a compound of formula 3:

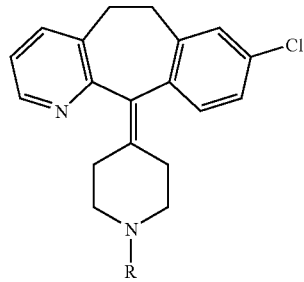

where R is —$COOR_1$, and $R_1$ is ethyl, in the presence of methanesulfonic acid for 5-15 hours at about 90° to 120° C. to produce desloratadine; and
    adjusting the pH of the hydrolysed reaction mixture to about 3 to 5;
    wherein the desloratadine is greater than 99.5% pure by HPLC and a 5% (w/v) solution of the desloratadine in methanol has an absorbance less than 0.15 AU at 420 nm.

2. The process of claim 1, further comprising purifying the desloratidine by:
    optionally, treating the pH adjusted reaction mixture with an adsorbent;
    adjusting the pH of the reaction mixture to greater than about 9; and
    isolating desloratadine by recrystallization from a solvent system comprising a mixture of an alcohol and a hydrocarbon solvent.

3. The process of claim 2, wherein adsorbent is selected from charcoal, neutral or alkaline alumina, silica and fuller's earth.

4. The process of claim 2, wherein the alcohol is methanol and the hydrocarbon solvent is cyclohexane.

5. The process of claim 4, wherein the ratio of methanol:cyclohexane is 1:14 v/v.

* * * * *